(12) United States Patent
Mulik et al.

(10) Patent No.: US 8,957,230 B2
(45) Date of Patent: Feb. 17, 2015

(54) SYNTHESIS OF CLEISTANTHIN A AND DERIVATIVES THEREOF

(76) Inventors: Nilesh Shridhar Mulik, Mumbai (IN); Kailash Dattatraya Panghavane, Mumbai (IN)

( * ) Notice: Subject to any disclaimer, the term of this patent is extended or adjusted under 35 U.S.C. 154(b) by 54 days.

(21) Appl. No.: 13/537,705

(22) Filed: Jun. 29, 2012

(65) Prior Publication Data

US 2013/0012727 A1 Jan. 10, 2013

Related U.S. Application Data

(60) Provisional application No. 61/503,136, filed on Jun. 30, 2011.

(51) Int. Cl.
| | | |
|---|---|---|
| C07D 407/04 | (2006.01) | |
| C07D 317/54 | (2006.01) | |
| C07D 407/14 | (2006.01) | |

(52) U.S. Cl.
CPC ............ C07D 317/54 (2013.01); C07D 407/14 (2013.01); C07D 407/04 (2013.01)
USPC ........................................................ 549/299

(58) Field of Classification Search
CPC .................................................. C07D 407/04
USPC ........................................................ 549/299
See application file for complete search history.

(56) References Cited

FOREIGN PATENT DOCUMENTS

| | | | |
|---|---|---|---|
| WO | 2004-093781 A2 | * | 11/2004 |
| WO | WO 2004/093781 A2 | | 11/2004 |
| WO | 2005-097767 A1 | * | 10/2005 |
| WO | WO 2005/097767 A1 | | 10/2005 |
| WO | 2008-058897 A2 | * | 5/2008 |
| WO | WO 2008/058897 A2 | | 5/2008 |
| WO | 2009-136889 A1 | * | 11/2009 |
| WO | WO 2009/136889 A1 | | 11/2009 |
| WO | 2010-089778 A2 | * | 8/2010 |
| WO | WO 2010/089778 A2 | | 8/2012 |

OTHER PUBLICATIONS

PCT/IB2012/001296, International Preliminary Report on Patentability, issued Jan. 7, 2014.
PCT/IB2012/001296, International Search Report, issued Feb. 5, 2013.
Charlton et al., "Hindered Rotation in Arylnaphthalene Lignans," J. Org. Chem. 1996, 61(10), 3452-3457.

* cited by examiner

*Primary Examiner* — Taofiq A Solola
(74) *Attorney, Agent, or Firm* — Cheryl H. Agris; Agris & van Natzme, LLP

(57) ABSTRACT

The present invention provides a method for preparing Cleistanthin A, a diphyllin glycoside, derivatives thereof and intermediates thereto. In particular the present invention provides in one of the aspect a method for synthesis of compound of formula D a key intermediate of diphyllin, which can be carried out in a shorter duration and at an ordinary temperature.

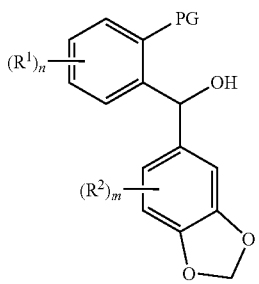

16 Claims, No Drawings

SYNTHESIS OF CLEISTANTHIN A AND DERIVATIVES THEREOF

RELATED APPLICATIONS

This application claims the benefit under 35 USC 119(e) of U.S. Provisional Patent Application No. 61/503,136, filed Jun. 30, 2011, the contents of which are hereby incorporated herein by reference in their entirety.

FIELD

The present invention relates to methods for synthesizing cleistanthin A, derivatives thereof, and to intermediates thereto.

BACKGROUND

Cleistanthin A (I) is a diphyllin glycoside isolated from the tropical plant *Cleistanthus collinus*:

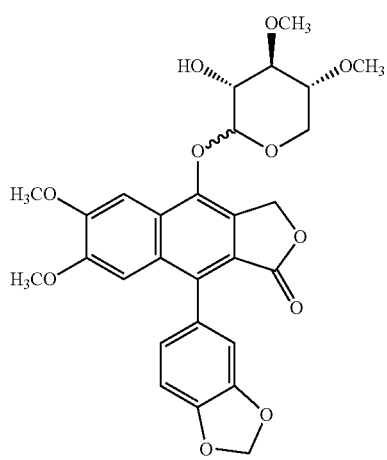

Cleistanthin A is a diphyllin glycoside having anticancer potential. It is found to arrest growth by inhibiting DNA synthesis and cancer cell division and by driving cancer cells to apoptosis. These properties of cleistanthin A renders it promising agent useful in regimens for treating. The conventional process for the isolation of cleistanthin A comprises the steps of treating the dried leaves of *Cleistanthus collinus* with petroleum ether to obtain a defatted powder, which is subsequently extracted with acetone and treated with benzene and chloroform to afford a black residue. Pure cleistanthin A is then isolated following recrystallization with acetone. Because such a process is lengthy and not sufficient for gram scale quantities, synthetic procedures have been developed which culminate in the glycosylation of diphyllin (II):

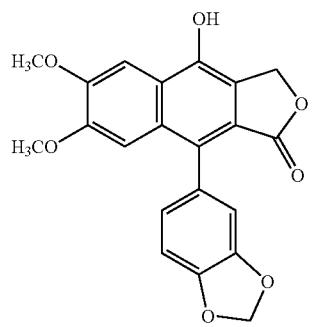

Diphyllin (II) is thus a key intermediate in the synthesis of cleistanthin A. The synthesis of diphyllin is reported in WO 2010/089778, the entirety of which is herein incorporated by reference. This synthesis, while accomplished in only five linear steps from commercially available starting material, includes a metallation step requiring extremely low temperatures. Such temperatures, while may be easy to carry out on small laboratory scale, are exponentially problematic on a commercial scale, requiring the use of hazardous reagents and long reaction times. Further, such conditions limit the scale on which a compound can be manufactured, ultimately increasing the production cost of the active pharmaceutical ingredient (API). Hence, there remains a need for a more robust, of shorter duration and commercially viable synthesis of diphyllin, its analogs and intermediates thereof.

SUMMARY

Accordingly, in one aspect the present invention provides a method for synthesis of an intermediate compound of diphyllin, which can be carried out in a shorter duration and at an ordinary temperature.

In one embodiment the present invention provides a method for synthesis of compound of formula D:

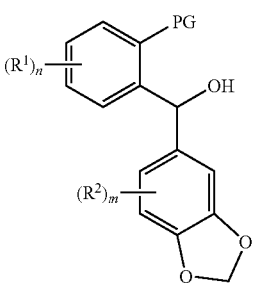

comprising the steps of:
(a) providing a solution of a compound of formula C:

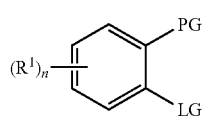

(b) sonicating said solution; and
(c) reacting said solution with an aryl aldehyde solution and an alkyl lithium reagent under sonication to form a compound of formula D. The compounds of formula D and C are described in detail herein below.

In another aspect, the present invention provides a method for synthesis of a diphyllin (II) or its derivatives, which can be carried out in a shorter duration and at an ordinary temperature.

In some embodiments the present invention provides a method for synthesis of compounds of formula III:

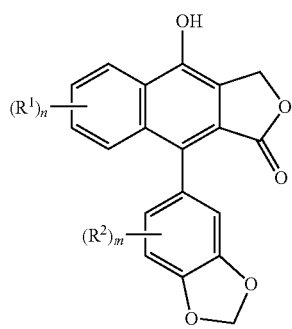

III comprising the steps of:
(a) reacting compound of formula D with a compound of formula E:

E under conditions effective to form a compound of formula F; and

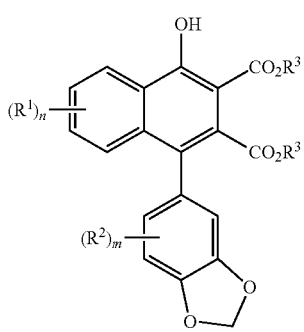

F (b) reacting said compound F with a metal hydride to form a compound of formula III The compounds of formula E, F and III are described in detail herein below.

In one embodiment said intermediate compound F is dimethyl 1-(benzo[d][1,3]dioxol-5-yl)-4-hydroxynaphthalene-2,3-dicarboxylate, the reduction of said dimethyl 1-(benzo[d][1,3]dioxol-5-yl)-4-hydroxynaphthalene-2,3-dicarboxylate with lithium aluminum hydride provides diphyllin (II).

In still another aspect the present invention provides a method for synthesis of an improved method for preparing an acetate derivative of Cleistanthin A.

In an embodiment, the present invention provides a method for preparing a compound of formula IV:

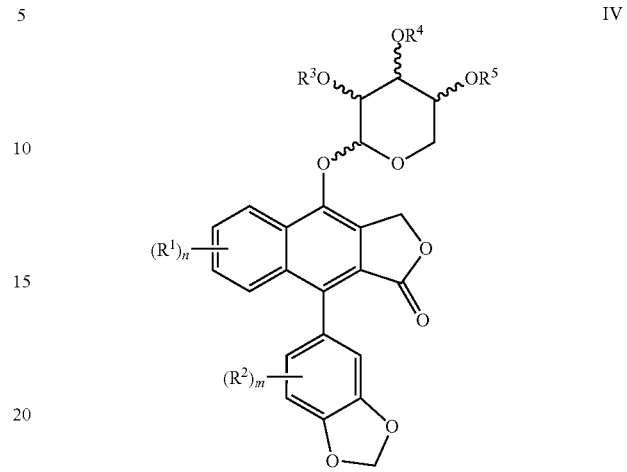

IV comprising the steps of:
(a) providing a compound of formula III:

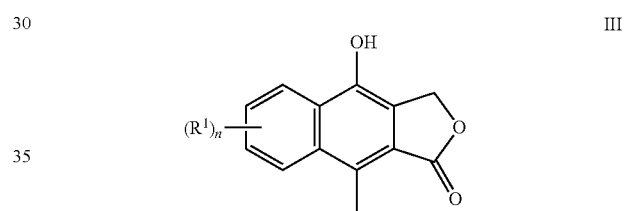

III and
(b) reacting said compound of formula III with a pyranose of formula V:

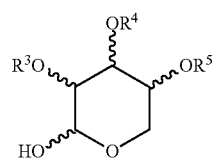

V under conditions effective to form a compound of formula IV. The compounds of formula III, IV and V are described in detail herein below.

In yet another aspect the present invention provides an improved method for preparing Cleistanthin A, which can be carried out in a shorter duration and wherein the metallation step is carried out at an ordinary temperature.

In one of the embodiment, the present invention provides a method for preparing Cleistanthin A (I):

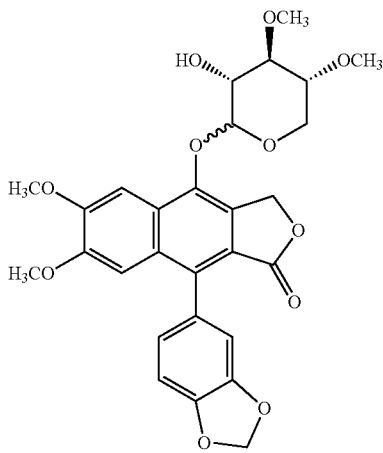

comprising a step of reacting compound of formula IV:

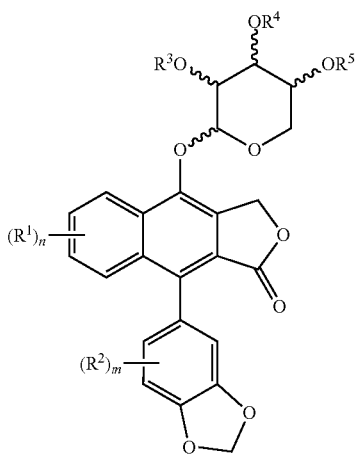

under conditions effective to form cleistanthin A (I). In one specific embodiment, the effective conditions include treating compound of formula iv with an alkali and a solvent to form compound of formula I.

DETAILED DESCRIPTION OF THE INVENTION

In general aspects the present invention provides methods for synthesizing cleistanthin A, derivatives thereof, and to intermediates thereto. Cleistanthin A is a diphyllin glycoside and one of the main step in synthesizing it, is glycosylation of an intermediate diphyllin. One key step in the synthesis of diphyllin is the condensation of an aryl lithium anion, formed from the reaction of an aryl lithium and an aryl aldehyde. Such aryl lithium anions are readily generated in situ via a lithium-halogen exchange from the treatment of an aryl halide with a lithium reagent. Lithium reagents are moisture-sensitive and/or pyrophoric, requiring the reactions to be conducted at very low temperatures. Moreover, because the reactivity of lithium reagents is in part due to their high nucleophilicity, they are prone to unwanted side reactions. Such side reactions include the $S_NAr$ addition of the alkyl lithium to the aryl halide, resulting in an alkylated aryl species rather than the desired aryl lithium anion. Alkylated aryl species account for the majority of byproducts associated with lithium-halogen exchange and render the starting material unusable. While the generation of such byproducts may be acceptable at the first step of a synthesis, it is particularly undesirable at later stages of a synthesis when advanced intermediates are converted to unusable materials. Thus, low temperatures are necessary to minimize both the hazards associated with the use of lithium reagents as well as the potential for side reactions. As discussed above, such temperatures, though may appear trivial on small scale, are much more difficult to reach, maintain and/or control at small as well as on a larger, commercial scale, thus rendering such reactions inefficient and costly.

It has now been surprisingly found that such condensations may be performed at higher temperatures. Moreover, such condensations run at higher temperatures result in fewer side reactions. Accordingly, the present invention provides methods of preparing compounds of formula III:

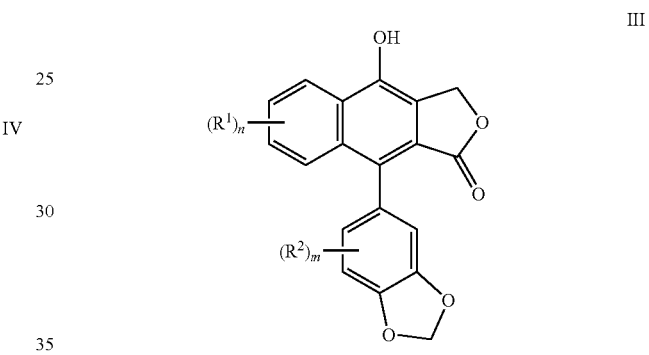

or a pharmaceutically acceptable salt thereof, wherein:
m is 0, 1, 2, or 3;
n is 0, 1, 2, 3, or 4;
each of $R^1$ and $R^2$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—; and
each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
  two R groups on the same nitrogen are taken together with their intervening atoms to form a 3-8 membered saturated, partially unsaturated, or aromatic ring having 1-4 heteroatoms independently selected from nitrogen, oxygen, or sulfur.

In particular, the present invention provides methods of preparing synthetic intermediates useful for preparing such compounds.

In certain embodiments, the present compounds are generally prepared according to Scheme I set forth below:

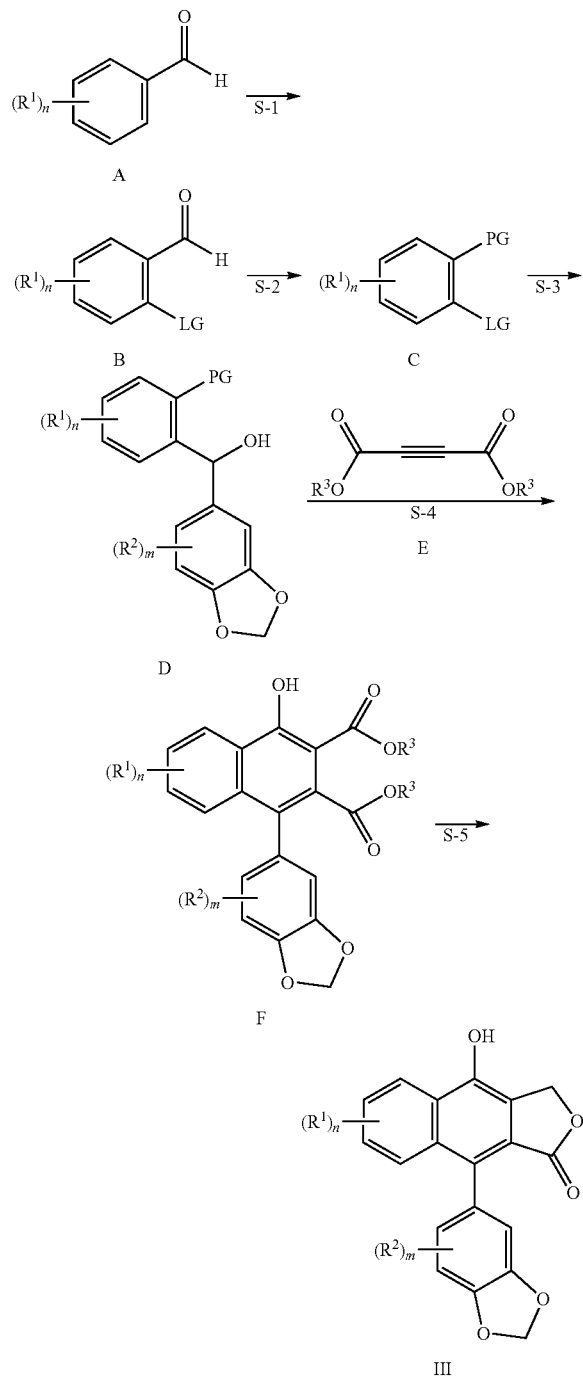

wherein each of $R^1$, $R^2$, $R^3$, n, m, PG, and LG are as defined and described in embodiments herein.

In one aspect, the present invention provides methods for preparing benzo[d][1,3]dioxol-5-yl(phenyl)methanol compounds of formula D according to the steps depicted in Scheme I, above. At step S-1, a leaving group, LG, is incorporated into intermediate A to form intermediate B. One of ordinary skill in the art will recognize that a variety of leaving groups are suitable for use in provided methods. As used herein, the term "leaving group" refers to a chemical moiety that is readily displaced by a desired incoming chemical moiety. Suitable leaving groups are well known to a person having ordinary skill in the art and can be selected suitably. Such leaving groups include halogens. In certain embodiments, LG is Bromine. In some embodiments, LG is iodine.

In some embodiments, n is 0, indicating a hydrogen at the $R^1$ position. In some embodiments, n is 1. In some embodiments, n is 2. In some embodiments, n is 3. In some embodiments, n is 4.

In some embodiments, $R^1$ is L-R. In some embodiments, $R^1$ is L-R, wherein L is a covalent bond.

In some embodiments, $R^1$ is L-R, wherein L is an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—. In some embodiments, $R^1$ is L-R, wherein L is an optionally substituted bivalent $C_{1-5}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—. In some embodiments, $R^1$ is L-R, wherein L is an optionally substituted bivalent $C_{1-4}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—. In some embodiments, $R^1$ is L-R, wherein L is an optionally substituted bivalent $C_{1-3}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—.

In some embodiments, $R^1$ is L-R, wherein L is an optionally substituted bivalent $C_{1-2}$ hydrocarbon chain, wherein one or both methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—.

In some embodiments, $R^1$ is L-R, wherein L is an optionally substituted bivalent $C_{1-2}$ hydrocarbon chain, wherein one methylene unit of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—.

In some embodiments, $R^1$ is L-R, wherein L is —O—.

In some embodiments, $R^1$ is L-R, wherein R is hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur.

In some embodiments, $R^1$ is L-R, wherein R is hydrogen. In some embodiments, $R^1$ is L-R, wherein L is a covalent bond and R is hydrogen.

In some embodiments, $R^1$ is L-R, wherein R is an optionally substituted group selected from $C_{1-6}$ aliphatic. In some embodiments, $R^1$ is L-R, wherein R is an optionally substituted group selected from $C_{1-5}$ aliphatic. In some embodiments, $R^1$ is L-R, wherein R is an optionally substituted group selected from $C_{1-4}$ aliphatic. In some embodiments, $R^1$ is L-R, wherein L is a covalent bond and R is n-butyl, sec-butyl or tert-butyl. In some embodiments, $R^1$ is L-R, wherein L is a covalent bond and R is —$CH_2CH_2CH_2CH_3$.

In some embodiments, $R^1$ is L-R, wherein R is an optionally substituted group selected from $C_{1-3}$ aliphatic. In some embodiments, $R^1$ is L-R, wherein L is a covalent bond and R is propyl or isopropyl. In some embodiments, $R^1$ is L-R, wherein L is a covalent bond and R is —$CH_2CH_2CH_3$.

In some embodiments, $R^1$ is L-R, wherein R is an optionally substituted group selected from $C_{1-2}$ aliphatic. In some embodiments, $R^1$ is L-R, wherein L is a covalent bond and R is —$CH_2CH_3$. In some embodiments, $R^1$ is L-R, wherein L is —O— and R is —$CH_2CH_3$.

In some embodiments, $R^1$ is L-R, wherein R is an optionally substituted methyl group. In some embodiments, $R^1$ is L-R, wherein L is a covalent bond and R is —$CH_3$.

In some embodiments, $R^1$ is L-R, wherein L is —O— and R is —$CH_3$.

In some embodiments, intermediate A is selected from:

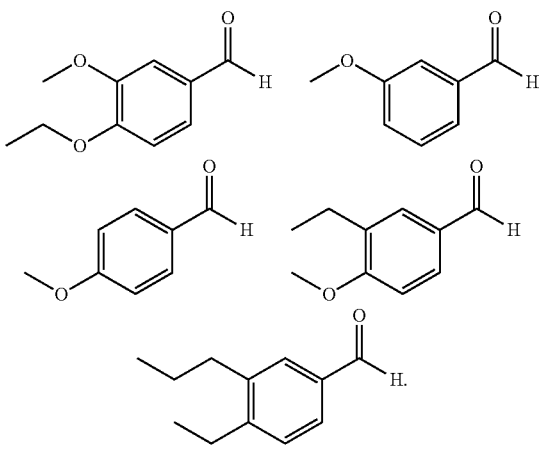

In some embodiments of S-1, such LG may be incorporated via an electrophilic aromatic substitution reaction. In some embodiments of S-1, a halogen LG is incorporated into intermediate A via an electrophilic aromatic substitution reaction. In some such embodiments of S-1, compounds of intermediate B are prepared by reacting intermediate A with $X_2$. In some embodiments, $X_2$ is $Cl_2$, $Br_2$ or $I_2$. In some embodiments of S-1, compounds of intermediate B are prepared by reacting intermediate A with $X_2$ in the presence of an acid. Suitable acids for use in step S-1 include, but are not limited to, mineral acids such as hydrochloric acid, as well as organic acids such as acetic acid. In some embodiments of step S-1, intermediate A is treated with $X_2$ in the presence of acetic acid. In certain embodiments, the electrophilic aromatic substitution of 3,4-dimethoxybenzaldehyde in the presence of bromine and acetic acid provides 2-bromo-4,5-dimethoxybenzaldehyde.

At step S-2, the aryl aldehyde is converted to a protecting group PG. The PG of intermediate C is a suitable carbonyl protecting group. Suitable carbonyl protecting groups are well known to a person having ordinary skill in the art and can be selected suitably by such a person. Suitable carbonyl protecting groups include, but are not limited to, cyclic and dialkyl acetals, monothioacetals or thioacetals. Cyclic acetals include 1,3-dioxolanes and 1,3-dioxanes. Cyclic thioacetals include 1,3-dithianes and 1,3-dithiolanes. In some embodiments of step S-2, the PG moiety of intermediate C is a 1,3-dioxolanyl moiety. In some embodiments of step S-2, the PG moiety of intermediate C is a 1,3-dioxanyl moiety. In some embodiments of step S-2, the PG moiety of intermediate C is a 1,3-dithiolanyl moiety. In some embodiments of step S-2, the PG moiety of intermediate C is a 1,3-dithianyl moiety. In some embodiments of step S-2, the PG moiety is —$CH(OCH_3)_2$. In some embodiments of step S-2, the PG moiety is —$CH(SCH_3)_2$. In some embodiments of step S-2, the PG moiety is —$CH(OC_2H_5)_2$. In some embodiments of step S-2, the PG moiety is —$CH(OC_3H_7)_2$. In certain embodiments, the present invention provides a method of preparing intermediate C by treating benzaldehyde B with ethylene glycol, or an equivalent thereof. In some embodiments, the present invention provides a method of preparing intermediate C by treating benzaldehyde B with a catalytic amount of acid and ethylene glycol, or an equivalent thereof. Suitable acids for catalyzing the condensation of ethylene glycol and an aldehyde include both mineral acids, such as hydrochloric acid, and organic acids, such as p-toluenesulfonic acid. In certain embodiments, the condensation of 2-bromo-4,5-dimethoxybenzaldehyde and ethylene glycol in the presence of catalytic p-toluenesulfonic acid provides 2-(2-bromo-4,5-dimethoxyphenyl)-1,3-dioxolane. One of ordinary skill will appreciate that the oxidation state of the aldehyde moiety in intermediate A can be modified so as to permit access to other starting materials of formula A. For example, in some embodiments, an appropriately substituted benzoic acid is subjected to electrophilic aromatic substitution conditions to provide the benzoic acid analog of intermediate B. The benzoic acid moiety is then protected as, for example, an orthoester to enable aryl lithium formation at step S-3. The orthoester PG is then deprotected and/or converted to an aldehyde or aldehydic oxidation state prior to or during step S-4.

At step S-3, the aryl ring of intermediate C is metallated with an alkyl lithium to form an aryl lithium anion in situ. Suitable alkyl lithiums for use in the present invention include n-butyllithium, sec-butyllithium and tert-butyllithium. In some embodiments, the aryl ring of formula C is treated with n-butyllithium.

The aryl anion formed from treating intermediate C with an alkyl lithium is thereby reacted with an aryl aldehyde to form intermediate D. In some embodiments, the aryl aldehyde is optionally substituted pipronal. As discussed above, such nucleophilic additions are generally performed at low temperatures, for example, at −70° C. Typically, reactions run at such low temperatures take 3 or more hours to achieved the desired temperature. Once the reaction has reached the target temperature, such as −70° C., the reaction temperature must be carefully maintained by slow addition of or to the electrophile.

Temperatures of about −60° C. to about −80° C. are generally achieved through the use of solid carbon dioxide (e.g., dry ice) or liquid nitrogen. Both of these reagents are hazardous on small scale, and the hazards which is only amplified on larger scales. For example, both dry ice and liquid nitrogen rapidly freeze or burn unprotected skin, resulting in frostbite. Further, dry ice readily sublimes at room temperature, releasing carbon dioxide gas into the air and displacing the oxygen in confined locations. Similarly, liquid nitrogen evaporates below room temperature and can also displace the oxygen in the air. Thus, both dry ice and liquid nitrogen can act as asphyxiates when used in poorly ventilated spaces. Further, both carbon dioxide and nitrogen are odorless, colorless and tasteless, and can asphyxiate a subject without any sensation or prior warning.

At temperatures of about −60° C. to about −80° C., a nucleophilic addition reaction such as step S-3 can require reaction times of at least 8-9 hours or longer, depending on the scale, as larger volumes require longer cooling times. Further, the temperature of larger volumes is more difficult maintain and control. Due to the difficulties in maintaining such a temperature, side reactions are common and result in higher percentages of impurities. Such impurities render the isolation of the product difficult and contribute to overall low yields.

Sonication is the agitatation of particles in a sample through the application of sound energy (i.e., ultrasound). It has now been surprisingly found that the use of sonication in the nucleophilic addition of the aryl lithium anion to the aryl aldehyde results in a cleaner reaction profile. Thus, in some embodiments, the present invention provides method of preparing a compound of intermediate D comprising a nucleophilic addition reaction of an aryl lithium anion to an aryl aldehyde, wherein the nucleophilic addition reaction is performed under sonication. It has further been surprisingly found that such a nucleophilic addition reaction can be run at room temperature, thereby decreasing the reaction times and eliminating the hazards associated with the use of dry ice and/or liquid nitrogen. Moreover, the impurities formed during sonication are minimal, thus demonstrating the enhanced selectivity of the reaction. Accordingly, in some embodiments, the present invention provides a method of preparing intermediate D comprising the nucleophilic addition of an aryl anion to an aryl aldehyde, wherein the nucleophilic addition is performed under sonication at room temperature. In certain embodiments, the nucleophilic addition of (2-(1,3-dioxolan-2-yl)-4,5-dimethoxyphenyl)lithium anion to pipronal provides (2-(1,3-dioxolan-2-yl)-4,5-dimethoxyphenyl)(benzo[d][1,3]dioxol-5-yl)methanol, wherein the nucleophilic addition is performed under sonication and at room temperature as per Scheme II.

Scheme II:

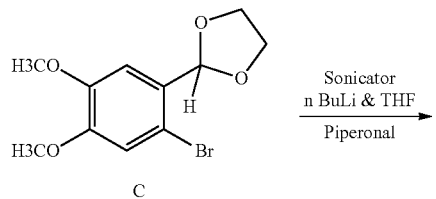

C

Sonicator
n BuLi & THF
Piperonal
→

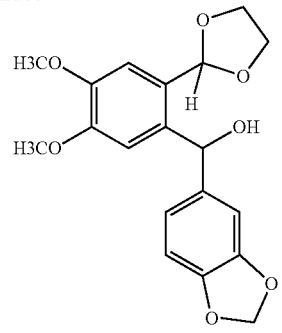

D

In some embodiments, such a sonication reaction is complete within 1-3 hours. Further, the use of sonication is environmentally friendly and doesn't generate waste (such as gaseous emissions and/or solvent waste) related to temperature control.

At step S-4, intermediate D is converted to an isobenzofuran moiety in situ, which then undergoes a cycloaddition reaction with dicarboxylacetylene intermediate E to afford intermediate F. See, for example, Charlton et al., "Hindered Rotation in Arylnaphthalene Lignans," *J. Org. Chem.* 1996, 61(10), 3452-3457. In some embodiments of step S-4, the cycloaddition reaction is a Diels-Alder reaction.

One of ordinary skill will recognize that a cycloaddition reaction such as step S-4 requires removal or unmasking of the PG (i.e. the aldehyde) to enable the formation of the isobenzofuran intermediate. Suitable conditions for removing the PG moiety in intermediate D are well known in the art. In some embodiments of step S-4, intermediate D is treated with an acid. Suitable acids for removing PG in step S-4 include organic acids and mineral acids. In some embodiments, intermediate D is treated with an organic acid. In some such embodiments, intermediate D is treated with acetic acid. In some embodiments, intermediate D is treated with a mineral acid. In some such embodiments, intermediate D is treated with hydrochloric acid. Thus, in some embodiments, the cycloaddition of an isobenzofuran and a dicarboxylacetylene moiety E in the presence of acetic acid provides the alkyl 1-(benzo[d][1,3]dioxol-5-yl)-4-hydroxynaphthalene-2,3-dicarboxylate F.

In some embodiments, intermediate D is treated with acid and heated to effect in situ generation of an isobenzofuran. One of ordinary skill in the art would recognize that a wide variety of acids are useful for deprotecting acid-sensitive acetal groups. In some such embodiments, intermediate D is treated with a mineral acid and heated. In some embodiments, intermediate D is treated with an organic acid and heated. In some embodiments, the Diels-Alder reaction of step S-4 is heated to a temperature of at least 100° C. in the presence of an organic acid. In some embodiments, the Diels-Alder reaction of step S-4 is heated to a temperature of at least 100° C. in the presence of acetic acid. In some embodiments, the Diels-Alder reaction of step S-4 is heated to a temperature of at least 120° C. in the presence of acetic acid. In some embodiments, the Diels-Alder reaction of step S-4 is heated to a temperature of at least 140° C. in the presence of acetic acid.

In some embodiments, each $R^3$ of intermediate E is independently an optionally substituted $C_{1-6}$ aliphatic. In some embodiments, each $R^3$ of intermediate E is independently an optionally substituted $C_{1-5}$ aliphatic. In some embodiments, each $R^3$ of intermediate E is independently an optionally substituted $C_{1-4}$ aliphatic. In some embodiments, each $R^3$ of intermediate E is independently an optionally substituted $C_{1-3}$ aliphatic. In some embodiments, each $R^3$ of intermediate E is an optionally substituted propyl group. In some embodiments, each $R^3$ of intermediate E is independently an optionally substituted $C_{1-2}$ aliphatic. In some embodiments, each $R^3$ of intermediate E is an optionally substituted ethyl group. In some embodiments, each $R^3$ of intermediate E is an optionally substituted methyl group. In some embodiments, each $R^3$ of intermediate E is —$CH_3$. In some embodiments, each $R^3$ of intermediate E is —$CH_2CH_3$. In some embodiments, each $R^3$ of intermediate E is —$CH_3$. In some embodiments, each $R^3$ of intermediate E is —$CH_2CH_2CH_3$.

In certain embodiments, the Diels-Alder reaction of 5-(5,6-dimethoxyisobenzofuran-1-yl)benzo[d][1,3]dioxole and diethyl acetylene-dicarboxylate in the presence of acetic acid and at 140° C. provides dimethyl 1-(benzo[d][1,3]dioxol-5-yl)-4-hydroxynaphthalene-2,3-dicarboxylate.

At step S-5, the naphthylenedicarboxylate F is treated with a metal hydride to effect the condensation-cyclization of the lactone moiety of intermediate III. One of ordinary skill in the art would recognize that the hydroxyl group of intermediate F controls the selectivity of the reduction through a six-membered coordination of the metal, directing reduction of the proximal carboxylate ester. Suitable metal hydrides useful in the selected reduction of intermediate F include borohydrides, boranes and aluminum hydrides. In some embodiments of step S-5, the metal hydride is selected from lithium aluminum hydride, diisobutylaluminum hydride, sodium borohydride, lithium borohydride, zinc borohydride and borane. In certain embodiments, the reduction of dimethyl 1-(benzo[d][1,3]dioxol-5-yl)-4-hydroxynaphthalene-2,3-dicarboxylate with lithium aluminum hydride provides diphyllin (II).

According to another aspect, the present invention provides a method for preparing a compound of formula IV:

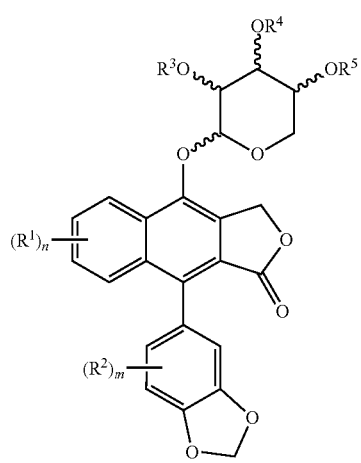

or a pharmaceutically acceptable salt thereof, wherein:
m is 0, 1, 2, or 3;
n is 0, 1, 2, 3, or 4;
each of $R^1$ and $R^2$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
two R groups on the same nitrogen are taken together with their intervening atoms to form a 3-8 membered saturated, partially unsaturated, or aromatic ring having 1-4 heteroatoms independently selected from nitrogen, oxygen, or sulfur; and each $R^3$, $R^4$ and $R^5$ is independently hydrogen, $R^6$, or —C(O)$R^6$;

each $R^6$ is independently an optionally substituted $C_{1-6}$ aliphatic group or a suitable hydroxyl protecting group;
comprising the steps of:
(a) providing a compound of formula III:

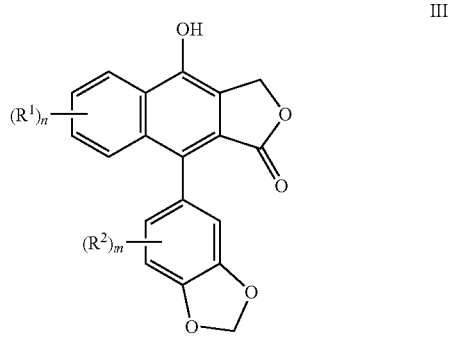

wherein each of n, m, $R^1$, and $R^2$ is as defined above and described herein, and
(b) reacting said compound of formula III with a pyranose of formula V:

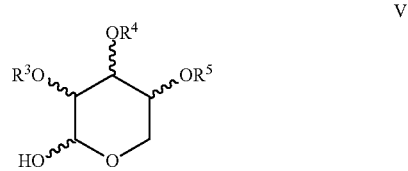

wherein each of $R^3$, $R^4$ and $R^5$ is independently hydrogen, $R^6$, or —C(O)$R^6$; and
each $R^6$ is independently an optionally substituted $C_{1-6}$ aliphatic group or a suitable hydroxyl protecting group;
under conditions effective to form a compound of formula IV.

The synthesis of compounds of formula V is set forth in assignee's PCT International Application WO 2010/089778, particularly in reaction scheme presented under the heading "Synthesis of Compound of Formula III" and described in lines 14-18 on page 8 to lines 1-20 on page 20 as well as illustrated in Example 4 on page 17 through page 20 the disclosure of which is incorporated herein in its entirety by reference. Said reaction scheme and description of the same from PCT International Application WO 2010/089778 is excerpted. "According to another embodiment of the present invention a process for preparing compound of formula III is represented as follows:

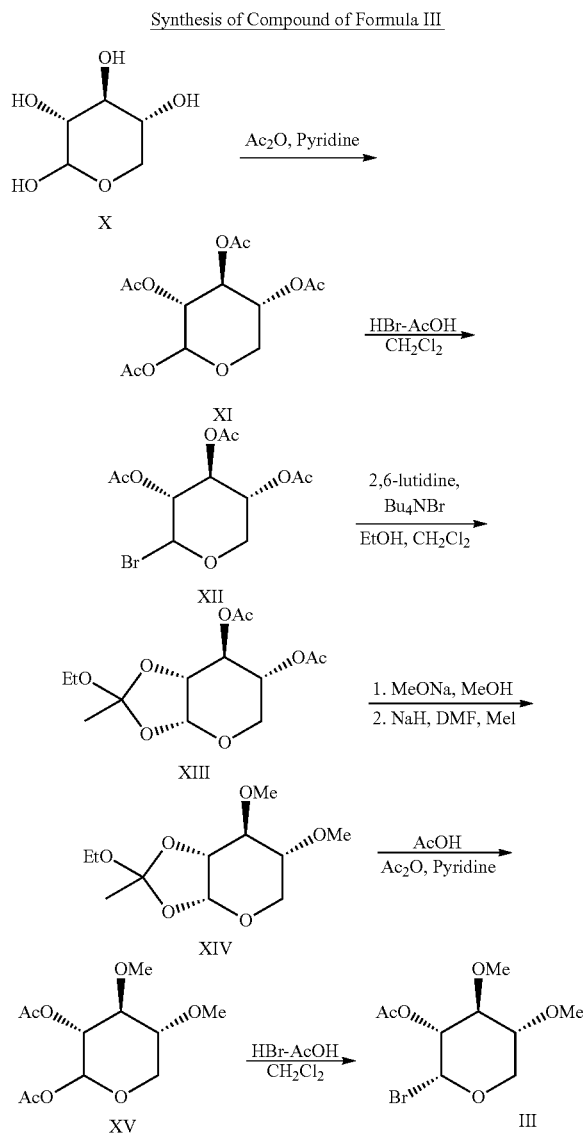

The process comprises the step of reacting a compound of formula X with pyridine. Acetic anhydride is added to the mixture to result in compound of formula XI. The temperature of the reaction mixture is maintained at 0° C. for 4-6 hours. Compound of formula XI is further treated with dichloromethane. The reaction mixture is cooled to 0° C. To this cold solution hydrogen bromide in acetic acid is added to form a compound of formula XII. The reaction is carried out for 1-3 hours. Compound of formula XII is treated with 2,6 lutidine, tetrabutyl ammonium bromide, anhydrous dichloromethane and ethanol at room temperature to form a compound of formula XIII Compound of formula XIII is treated with methanol and sodium methoxide to obtain a residue. The reaction is carried at room temperature for 1-2 hours. The residue is dissolved in dimethyl formamide and the mixture is cooled to 0 deg C. To the resulting solution sodium hydride is added to form a suspension. Methyl iodide is further added to the resulting suspension to form compound of formula XIV. Compound of formula XIV is dissolved in acetic acid and the reaction mixture is concentrated to obtain a residue. The temperature is maintained at 0° C. for 1-2 hours. The residue obtained is further treated with acetic anhydride and pyridine at room temperature to form compound of formula XV. Compound of formula XV is dissolved in dichloromethane. The reaction mixture is cooled to 0° C. To the cooled solution, hydrogen bromide in acetic acid is added to from compound of formula III. The reaction time is 2-3 hours. The compound of formula X is D-xylose. The compound of formula XI is Tetra-O- acetyl-D-xylopyranose. The compound of formula XII is 2,3,4-Tri-O-acetyl-α-D-bromoxylopyranose. The compound of formula XIII is 3,4-Di-0-acetyl-1,2-0-(1-ethoxyethylidene)-D-xylopyranose. The compound of formula XIV is 1,2-0-(1-Ethoxyethylidene)-3,4-dimethoxy-D-xylopyranose.

According to one embodiment, conditions effective to form a compound of formula III include a base. One of ordinary skill will recognize that a variety of bases are suitable for use in step (b) above. Suitable bases include inorganic or mineral bases, such as hydroxides, and organic bases such as alkyl amines and alkoxides. In some embodiments, a compound of formula III is reacted with a compound of formula V in the presence of sodium hydroxide. In some such embodiments, the sodium hydroxide is aqueous. In some embodiments, a compound of formula III is reacted with a compound of formula V in the presence of a 2 molar aqueous solution of sodium hydroxide.

One of ordinary skill will recognize that a compound of formula III is not soluble in an aqueous solution of sodium hydroxide. One of ordinary skill in the art will further recognize that the use of aqueous sodium hydroxide in step (b) above requires a phase transfer reagent. Thus, in some embodiments, one or more phase transfer reagents are utilized in step (b) above. Suitable phase transfer reagents include tetraalkylammonium salts such as tetrabutylammonium salts. In some embodiments, a compound of formula III is reacted with a compound of formula V in the presence of aqueous sodium hydroxide and tetrabutylammonium bromide.

In some embodiments, the present invention provides a method for preparing a compound of formula III:

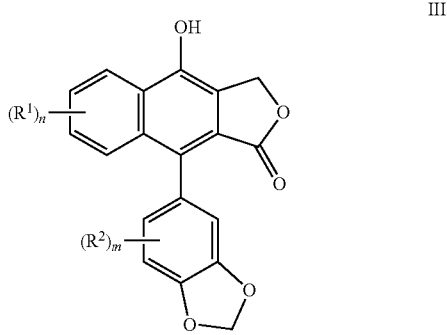

wherein:

m is 0, 1, 2, or 3;

n is 0, 1, 2, 3, or 4;

each of $R^1$ and $R^2$ is independently selected from halogen, —$NO_2$, —CN, or -L-R;

each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur; and comprising the steps of:

(a) providing a compound of formula F:

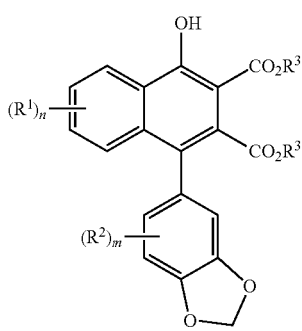

F wherein m is 0, 1, 2, or 3;

n is 0, 1, 2, 3, or 4;

each of $R^1$ and $R^2$ is independently selected from halogen, —$NO_2$, —CN, or -L-R;

each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur;

each $R^3$ is an optionally substituted aliphatic; and (b) reacting said compound F with a metal hydride to form a compound of formula III.

As described above, suitable metal hydrides for use in step (b) above include aluminum hydrides, borohydrides and boranes. In some embodiments, the metal hydride is selected from lithium aluminum hydride, diisobutylaluminum hydride, sodium borohydride, lithium borohydride, zinc borohydride and borane. In some embodiments, the metal hydride for use in step (b) is lithium aluminum hydride. One of ordinary skill will recognize that two molar equivalents of hydride are necessary to effect the reduction of the carboxylate proximal to the hydroxyl group on the naphthalene ring ("the proximal carboxylate"). One of ordinary skill will further recognize that many metal hydride reagents have two or more hydrides which may be transferred to a compound of formula F. Thus, in some embodiments, less than two molar equivalents of a metal hydride reagent is required to completely reduce the proximal carboxylate.

One of ordinary skill in the art will also appreciate that the treatment of a compound of formula F with a base such as a metal hydride will result in the immediate deprotonation of the hydroxyl group. Accordingly, in some embodiments of step (b) above, a compound of formula F is treated with at least two molar equivalents of a metal hydride to provide a compound of formula III. In some embodiments of step (b) above, a compound of formula F is treated with at least two molar equivalents of lithium aluminum hydride, wherein the first equivalent of the metal hydride is consumed by the deprotonation of the hydroxyl group and the second equivalent is effective to reduce the proximal carboxylate.

One of ordinary skill in the art will recognize that reactive reagents such as metal hydrides require the use of a non polar, aprotic solvent. Suitable non polar, aprotic solvents for use in step (b) above include ethers such as diethyl ether, tetrahydrofuran, dioxane and MTBE and hydrocarbon solvents such as hexanes or cyclohexane.

In some embodiments, step S-5 is performed at a temperature range of about −10° C. to about 0° C. In some embodiments, step S-5 is performed at room temperature.

In some embodiments, the present invention provides a method for preparing a compound of formula F:

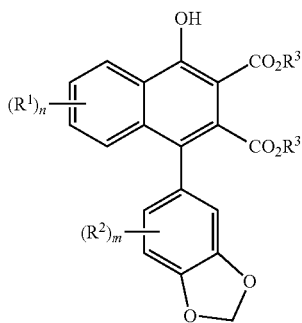

wherein:
m is 0, 1, 2, or 3;
n is 0, 1, 2, 3, or 4;
each of $R^1$ and $R^2$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —$S(O)_2$—, —$S(O)_2$N(R)—, —N(R)$S(O)_2$—, —OC(O)— or —C(O)O—;
each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
two R groups on the same nitrogen are taken together with their intervening atoms to form a 3-8 membered saturated, partially unsaturated, or aromatic ring having 1-4 heteroatoms independently selected from nitrogen, oxygen, or sulfur; and
each $R^3$ is independently an optionally substituted $C_{1-6}$ aliphatic;
comprising the steps of:
(a) providing a compound of formula D:

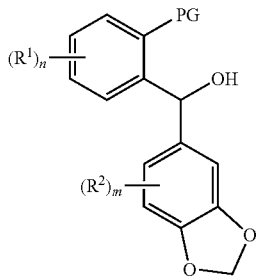

wherein:
m is 0, 1, 2, or 3;
n is 0, 1, 2, 3, or 4;
each of $R^1$ and $R^2$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —$S(O)_2$—, —$S(O)_2$N(R)—, —N(R)$S(O)_2$—, —OC(O)— or —C(O)O—;
each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
two R groups on the same nitrogen are taken together with their intervening atoms to form a 3-8 membered saturated, partially unsaturated, or aromatic ring having 1-4 heteroatoms independently selected from nitrogen, oxygen, or sulfur; and
PG is —CH($OR^3$), 2-(1,3-dioxolanyl) or 2-(1,3-dioxanyl);
(b) reacting said compound of formula D with a compound of formula E:

wherein each $R^3$ is an optionally substituted $C_{1-6}$ aliphatic;
(c) under conditions effective to form a compound of formula F.

As described above, the reaction of a compound of formula D and a compound of formula E is a cyclization reaction. In particular, such a reaction is a Diels-Alder reaction. As further described above, one of ordinary skill will recognize that the diene component of the Diels-Alder reaction is an isobenzofuran, which is generated in situ from a compound of formula D. In some embodiments, conditions effective to generate an isobenzofuran in situ from a compound of formula D include heating a compound of formula D in the presence of an acid. One of ordinary skill in the art will recognize that a variety of acids are useful to promote and/or facilitate such a reaction. Suitable acids include, without limitation, acetic acid, hydrochloric acid, p-toluenesulfonic acid, and the like. In some embodiments, a compound of formula D is treated with acetic acid.

One of ordinary skill in the art will recognize that a reaction such as the Diels-Alder reaction described above is performed at a temperature range of about 100° C. to about 200° C. In some embodiments, step (c) above is performed using acetic acid at a temperature of about 100° C. In some embodiments, step (c) above is performed using acetic acid at a temperature of about 120° C. In some embodiments, step (c) above is performed using acetic acid at a temperature of about 140° C. In some embodiments, step (c) above is performed using acetic acid at a temperature of at least 140° C.

One of ordinary skill will appreciate that suitable solvents for use in step (c) above include those which have a boiling point at or greater than 100° C. Suitable solvents useful in the present invention include polar, protic solvents such acetic acid and high-boiling alcohols, benzene and its derivatives (e.g. toluene, xylenes), dimethylformamide, dimethylacetamide and diglyme. In some embodiments, step (c) above is performed in acetic acid.

In some embodiments, a suitable solvent includes halogenated hydrocarbon solvents such as chloroform or methylene chloride, ethers such as diethyl ether or tetrahydrofuran and hydrocarbon solvents such as hexanes or cyclohexane.

In some embodiments, one or more reagents may perform as a suitable solvent.

In certain embodiments, the present invention provides a method for preparing a compound of formula D:

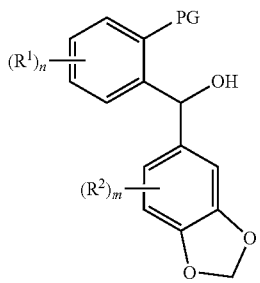

wherein:
m is 0, 1, 2, or 3;
n is 0, 1, 2, 3, or 4;
each of $R^1$ and $R^2$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;
each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
two R groups on the same nitrogen are taken together with their intervening atoms to form a 3-8 membered saturated, partially unsaturated, or aromatic ring having 1-4 heteroatoms independently selected from nitrogen, oxygen, or sulfur; and
PG is selected from —CH(OR$^8$)$_2$, —CH(SR$^8$)$_2$, 2-(1,3-dioxolanyl), 2-(1,3-dioxanyl), 2-(1,3-dithiolanyl) or 2-(1,3-dithianyl); and
$R^8$ is an optionally substituted $C_{1-6}$ aliphatic group;
comprising the steps of:
(a) providing a solution of:
a compound of formula C:

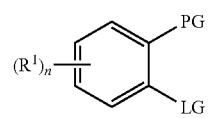

wherein
n is 0-4;
each $R^1$ is independently selected from halogen, —$NO_2$, —CN, or -L-R;
each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;
each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:
two R groups on the same nitrogen are taken together with their intervening atoms to form a 3-8 membered saturated, partially unsaturated, or aromatic ring having 1-4 heteroatoms independently selected from nitrogen, oxygen, or sulfur;
PG is selected from —CH(OR$^8$)$_2$, —CH(SR$^8$)$_2$, 2-(1,3-dioxolanyl), 2-(1,3-dioxanyl), 2-(1,3-dithiolanyl) or 2-(1,3-dithianyl); $R^8$ is an optionally substituted $C_{1-6}$ aliphatic group; and
LG is halogen;
(b) sonicating said solution; and
(c) reacting said solution with an aryl aldehyde solution and an alkyl lithium reagent under sonication to form a compound of formula D.

As described above, the reaction of an aryl halide of formula C with an alkyl lithium reagent to form an aryl lithium anion is generally performed at low temperatures to avoid unwanted side reactions. Such temperatures are typically −65° C. to about −80° C. In some embodiments, step (c) above is performed at temperatures above −65° C. In some embodiments, step (c) above under sonication is performed at temperatures within the range of about 0° C. to about 25° C. In some embodiments, step (c) above is performed at room temperature for example about 25° C. to about 35° C. under sonication.

As described above, suitable alkyl lithium reagents include n-butyllithium, sec-butyllithium and tert-butyllithium. In some embodiments, the alkyl lithium reagent n-butyllithium.

In some embodiments, the present invention provides a method of preparing a compound of formula D comprising the steps of (a) providing a solution of a compound of formula C, (b) sonicating said solution, and (c) reacting said solution with an aryl aldehyde solution and an alkyl lithium reagent to form a compound of formula D. In some embodiments, the aryl aldehyde is pipronal.

One of ordinary skill will appreciate that such reactions require the use of non polar, aprotic solvents. Suitable non polar, aprotic solvents include ethers such as diethyl ether, MTBE, tetrahydrofuran or dioxane or hydrocarbon solvents such as hexanes or cyclohexane.

In some embodiments, the present invention provides a method for preparing a compound of formula C:

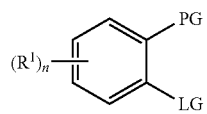

C wherein:

each $R^1$ is independently selected from halogen, —$NO_2$, —CN, or -L-R;

each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur;

PG is selected from —CH(OR$^8$)$_2$, —CH(SR$^8$)$_2$, 2-(1, 3-dioxolanyl), 2-(1,3-dioxanyl), 2-(1,3-dithiolanyl) or 2-(1,3-dithianyl); R$^8$ is $C_{1-6}$ aliphatic; and LG is halogen;

comprising the steps of:

(a) providing a compound of formula B:

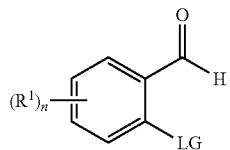

B wherein:

n is 0-4;

each $R^1$ is independently selected from halogen, —$NO_2$, —CN, or -L-R;

each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur;

LG is halogen, and (b) reacting said compound of formula B with an alcohol to form a compound of formula C, wherein the alcohol is selected from:

HOR$^8$, ethylene glycol, HSR$^8$, 1,3-propanediol, 1,2-ethanedithiol or 1,3-propanedithiol, wherein R$^8$ is $C_{1-6}$ aliphatic.

In some embodiments, step (b) above is performed using a catalytic amount of an acid. Suitable catalytic acids include both mineral acids, such as hydrochloric acid, and organic acids, such as p-toluenesulfonic acid. In some embodiments, step (b) is performed using p-toluenesulfonic acid.

In some embodiments, step (b) above is performed using methanol or ethanol. Thus, in some embodiments, a compound of formula B is reacted with methanol or ethanol to provide a compound of formula C wherein PG is —CH(OCH$_3$)$_2$ or —CH(OCH$_2$CH$_3$)$_2$, respectively. In some embodiments, a compound of formula B is reacted with ethylene glycol to provide a compound of formula C wherein PG is -2-(1,3-dioxolanyl). In some embodiments, a compound of formula B is reacted with 1,3-propanediol to provide a compound of formula C wherein PG is -2-(1,3-dioxanyl). In some embodiments, a compound of formula B is reacted with CH$_3$SH to provide a compound of formula C wherein PG is —CH(SCH$_3$)$_2$. In some embodiments, a compound of formula B is reacted with CH$_3$CH$_2$SH to provide a compound of formula C wherein PG is —CH(SCH$_2$CH$_3$)$_2$.

In some embodiments, a compound of formula B is reacted with 1,2-ethanedithiol to provide a compound of formula C wherein PG is 1,3-dithiolanyl. In some embodiments, a compound of formula B is reacted with 1,3-propanedithiol to provide a compound of formula C wherein PG is 1,3-dithianyl.

A suitable solvent or solvent mixture is selected such that the solvent solubilizes the reaction components and/or facilitates the progress of the reaction. Suitable solvents include halogenated hydrocarbon solvents (e.g. chloroform or methylene chloride), benzene and derivatives thereof (e.g., toluene, xylenes), ethers (e.g. MTBE, tetrahydrofuran and dioxane), and the like. In some embodiments, a suitable solvent is a polar, aprotic solvent such as tetrahydrofuran or dioxane.

According to one embodiment, the alcohol of step (b) above performs as the reaction solvent. When ethylene glycol or 1,3-propanediol is used as a solvent, one of ordinary skill in the art will appreciate that the reaction mixture is poured into a non-miscible organic solvent such as ethyl acetate or methylene chloride. The non-miscible organic layer is then washed with water to remove the excess alcohol.

In some embodiments, the reaction of a compound of formula B with an alcohol in the presence of catalytic acid is heated. In some embodiments, the reaction mixture is refluxed. In some embodiments, step S-2 is heated to about 90° C. to about 95° C.

In some embodiments, the present invention provides a method for preparing a compound of formula B:

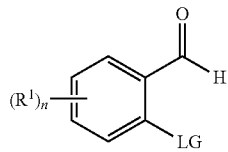

wherein n is 0-4;

each $R^1$ is independently selected from halogen, —$NO_2$, —CN, or -L-R;

each L is independently a covalent bond or an optionally substituted bivalent $C_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—, —S(O)—, —S(O)$_2$—, —S(O)$_2$N(R)—, —N(R)S(O)$_2$—, —OC(O)— or —C(O)O—;

each R is independently hydrogen or an optionally substituted group selected from $C_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur; and LG is halogen, comprising the steps of:

(a) providing a compound of formula A:

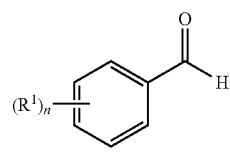

and (b) reacting said compound of formula A with a dihalogen to form a compound of formula B.

In some embodiments, a compound of formula A is reacted with chlorine gas, bromine or iodine. In some embodiments, a compound of formula A is reacted with bromine. In some embodiments, a compound of formula A is reacted with hydrobromic acid. In some embodiments, a compound of formula A is reacted with N-bromosuccinimide. In some embodiments, step (b) is performed in a polar, protic solvent. Suitable polar, protic solvents include alcohols (e.g. methanol, ethanol, isopropanol), organic acids (acetic acid, formic acid, propionic acid) and water. In some embodiments, a compound of formula A is dissolved in acetic acid and treated with bromine.

One of ordinary skill in the art will recognize that, in some circumstances, electrophilic aromatic substitutions require elevated temperatures. In some embodiments, a compound of formula A is dissolved in acetic acid and treated with bromine at room temperature.

In one of the embodiment, the present invention provides a method for preparing Cleistanthin A (I):

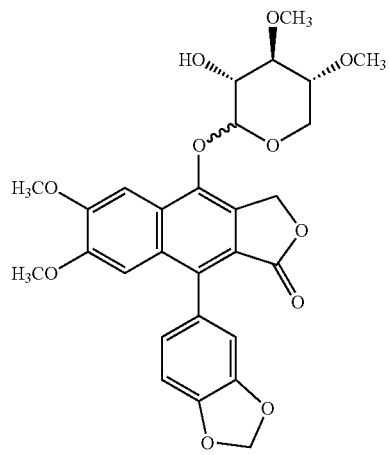

comprising a step of reacting compound of formula IV:

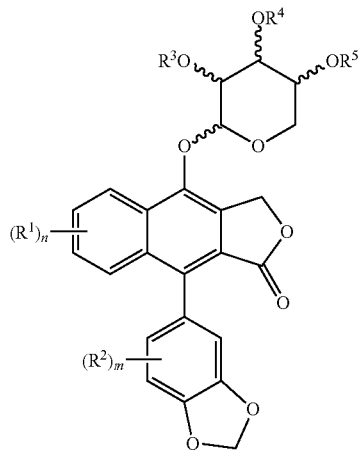

under conditions effective to form Cleistanthin A (I). In one specific embodiment, the effective conditions include treating compound of formula IV with an alkali and a solvent to form compound of formula I. One of ordinary skill will further recognize that many alkalis and solvents can be used in this reaction. In a preferred embodiment alkali is potassium carbonate and solvent is methanol.

The present invention provides an improved method for preparing Cleistanthin A, derivatives thereof and intermediates thereto, which can be carried out in a shorter duration and wherein the metallation step is carried out at an ordinary temperature. The metallation step is carried out in much shorter duration of 1-3 hours, preferably metallation step is carried out in 0.5-1 hour, thus shortening the period of the entire synthesis method and rendering it efficient.

The following examples serve to illustrate the invention without liming the scope thereof:

EXAMPLES

Synthesis of (2-(1,3-dioxolan-2-yl)-4,5-dimethoxyphenyl)(benzo[d][1,3]dioxol-5-yl)methanol—General Procedure A clean and dry four necked round bottom flask equipped with a thermometer pocket, water condenser and dropping funnel was placed in a sonicator. The flask was charged with dry tetrahydrofuran and 2-(2-bromo-4,5-dimethoxy)-1,3-dioxolane. The reaction was sonicated at room temperature. Pipronal dissolved in tetrahydrofurna was slowly charged via dropping funnel. n-Butyllithium was simultaneously charged to the reaction. The reaction was maintained at room temperature for 15 minutes and monitored by TLC. Once the reaction was complete, water was added and the reaction mixture was stirred. The organic layer was separated and concentrated under vacuum. Methanol was added to the sticky residue and the flask was scratched to initiate crystallization. The solid was filtered, washed with methanol and dried in a vacuum oven at 50° C. The isolated product was obtained in 36.9% yield.

Comparative Example 1A

Synthesis of (2-(1,3-Dioxolane-2-yl)-4,5-dimethoxy phenyl)(benzo(d)(1,3)dioxol-5-yl)-methanol (carried out as per known method):

To a flame dried four necked round bottom flask (100 mL) were added 2-(2-bromo-4,5-dimethoxyphenyl)-1,3-dioxolane (formula VII; 1.0 g, 0.9934 mole) and anhydrous tetrahydrofuran (25 ml) under nitrogen atmosphere. The flask was cooled to −78° C. in dry ice-acetone bath; n-Butyllithium (5.3 ml, 0.005 mole) was added drop wise with stirring at −78° C. and stirred for 15 minutes. A separate flame dried flask was charged with Piperonal (0.517 g, 1.0034 mole) and dry tetrahydrofuran (6 ml). The Piperonal solution was cannulated to the reaction mixture during 30 minutes and after the addition, reaction mixture was slowly warmed to room temperature and further stirred for 2.5 hours. After the consumption of all bromine compound, as confirmed by TLC (50:50, EtOAc:Hexane), reaction mixture was quenched by the addition of saturated ammonium chloride solution and extracted with ethyl acetate (3×20 ml). All the organic layers were combined, dried over anhydrous sodium sulfate, filtered and concentrated to yield 80% of crude product. The crude product was purified by column chromatography using column of 2 meter length, diameter 2.5 cm and filled with silica gel 60-120 (column chromatographic grade). Finally column eluted with EtOAC:Hexane (50:50), to get pure product (2-(1,3-Dioxolane-2-yl)-4,5-dimethoxy phenyl) (benzo(d)(1,3) dioxol-5-yl)-methanol with 30% yield. The total time required was about 7 hours.

The NMR details of compound (2-(1,3-Dioxolane-2-yl)-4, 5-dimethoxy phenyl)(benzo(d)(1,3)dioxol-5-yl)-methanol were as follows:

$^1$HNMR (300 MHz, CDCl$_3$): δ=7.14 (s, 1H), 6.90-6.78 (m, 4H), 6.11 (s, 1H), 5.96 (s, 2H), 5.90 (s, 1H), 4.19 (t, 2H, J=6.6 Hz), 4.16 (t, 2H, J=6.8 Hz), 4.02 (s, 3H), 3.81 (s, 3H, 3.17 (s, 1H). 13CNMR (300 MHz, CDCl3): δ=149.42, 148.11, 147.57, 146.58, 136.95, 135.43, 126.83, 121.04, 119.69, 111.48, 109.50, 107.92, 107.26, 101.65, 100.93, 71.34, 65.05, 55.94, 55.89.

Example 1

Synthesis of (2-(1,3-Dioxolane-2-yl)-4,5-dimethoxy phenyl)(benzo(d)(1,3)dioxol-5-yl)-methanol (carried out as per the present invention):

A clean, dry four neck round bottom flask equipped with mechanical stirrer, thermometer pocket, condenser, guard tube and dropping funnel was arranged on sonicator. It was charged with dry tetrahydrofuran (120 ml) and 2-(2-bromo-4, 5-dimethoxy)-1,3-dioxalane (5 gm, 0.017 mol). Said reaction mass was sonicated at temperature 25° C. Pipronal (3 g, 0.019 mol) previously dissolved in 10 ml tetrahydrofuran, was added by dropping funnel, simultaneously n-Butyllithium (20 g, 0.3125 mol) was slowly added to the reaction mixture under sonication at room temperature within 45 minutes. Following the addition, the reaction was monitored by TLC (50:50, EtOAc:Hexane), saturated ammonium chloride solution was added and extracted with ethyl acetate (2×30 mL). After completion of the reaction, 20 ml water was added, all organic layers were separated dried over anhydrous sodium sulphate, filtered and concentrated under vacuum to afford a sticky solid. Methanol (10 ml) was added and the flask was scratched to initiate crystallization. 2.3 g solid was isolated and dried under vacuum at 50° C. The isolated product was obtained in 37.55% yield. The NMR details of compound (2-(1,3-Dioxolane-2-yl)-4,5-dimethoxy phenyl) (benzo(d)(1,3)dioxol-5-yl)-methanol were as below:

$^1$HNMR (300 MHz, CDCl$_3$): δ=7.14 (s, 1H), 6.90-6.78 (m, 4H), 6.11 (s, 1H), 5.96 (s, 2H), 5.90 (s, 1H), 4.19 (t, 2H, J=6.6 Hz), 4.16 (t, 2H, J=6.8 Hz), 4.02 (s, 3H), 3.81 (s, 3H, 3.17 (s, 1H). 13CNMR (300 MHz, CDCl3): δ=149.42, 148.11, 147.57, 146.58, 136.95, 135.43, 126.83, 121.04, 119.69, 111.48, 109.50, 107.92, 107.26, 101.65, 100.93, 71.34, 65.05, 55.94, 55.89.

Example 2

Synthesis of (2-(1,3-Dioxolane-2-yl)-4,5-dimethoxy phenyl)(benzo(d)(1,3)dioxol-5-yl)-methanol (carried out as per the present invention):

A clean, dry four neck round bottom flask equipped with mechanical stirrer, thermometer pocket, condenser, guard tube and dropping funnel was arranged on sonicator. It was charged with dry tetrahydrofuran (120 ml) and 2-(2-bromo-4,5-dimethoxy)-1,3-dioxalane (5 gm, 0.0172 mol). Said reaction mass was sonicated at temperature 25° C. Pipronal (2.55 g, 0.0169 mol) previously dissolved in 10 ml tetrahydrofuran, was added by dropping funnel, simultaneously n-Butyl-lithium (3.96 g, 0.061 mole) was slowly added to the reaction mixture under sonication at room temperature within 50 minutes. Following the addition, the reaction was monitored by TLC (50:50, EtOAc:Hexane), after the consumption of all bromine compound, saturated ammonium chloride solution was added and extracted with ethyl acetate (3×30 ml). After completion of the reaction, 20 ml water was added, all organic layers were separated dried over anhydrous sodium sulphate, filtered and concentrated under vacuum to afford a sticky solid. Methanol (30 ml) was added and the flask was scratched to initiate crystallization. 2.3 g solid was isolated and dried under vacuum at 50° C. The isolated product was obtained in 36.55% yield.

The NMR details of compound (2-(1,3-Dioxolane-2-yl)-4,5-dimethoxy phenyl)(benzo(d)(1,3)dioxol-5-yl)-methanol were as below:

$^1$HNMR (300 MHz, CDCl$_3$): δ=7.14 (s, 1H), 6.90-6.78 (m, 4H), 6.11 (s, 1H), 5.96 (s, 2H), 5.90 (s, 1H), 4.19 (t, 2H, J=6.6 Hz), 4.16 (t, 2H, J=6.8 Hz), 4.02 (s, 3H), 3.81 (s, 3H, 3.17 (s, 1H). 13CNMR (300 MHz, CDCl3): δ=149.42, 148.11, 147.57, 146.58, 136.95, 135.43, 126.83, 121.04, 119.69, 111.48, 109.50, 107.92, 107.26, 101.65, 100.93, 71.34, 65.05, 55.94, 55.89.

Example 3

Synthesis of (2-(1,3-Dioxolane-2-yl)-4,5-dimethoxy phenyl) (benzo(d)(1,3)dioxol-5-yl)-methanol (carried out as per the present invention):

A clean, dry four neck round bottom flask equipped with mechanical stirrer, thermometer pocket, condenser, guard tube and dropping funnel was arranged on sonicator. It was charged with dry tetrahydrofuran (120 ml) and 2-(2-bromo-4,5-dimethoxy)-1,3-dioxalane (5 gm, 0.0172 mol). Said reaction mass was sonicated at temperature 30° C. Pipronal (2.55 g, 0.0169 mol) previously dissolved in 10 ml tetrahydrofuran, was added by dropping funnel, simultaneously n-Butyl-lithium (3.96 g, 0.061 mole) was slowly added to the reaction mixture under sonication at room temperature within 50 minutes. Following the addition, the reaction was monitored by TLC (50:50, EtOAc:Hexane), after the consumption of all bromine compound, saturated ammonium chloride solution was added and extracted with ethyl acetate (3×30 ml). After completion of the reaction, 20 ml water was added, all organic layers were separated dried over anhydrous sodium sulphate, filtered and concentrated under vacuum to afford a sticky solid. Methanol (30 ml) was added and the flask was scratched to initiate crystallization. 2.3 g solid was isolated and dried under vacuum at 50° C. The isolated product was obtained in 37% yield.

The NMR details of compound (2-(1,3-Dioxolane-2-yl)-4,5-dimethoxy phenyl)(benzo(d)(1,3)dioxol-5-yl)-methanol were as below:

$^1$HNMR (300 MHz, CDCl3): δ=7.14 (s, 1H), 6.90-6.78 (m, 4H), 6.11 (s, 1H), 5.96 (s, 2H), 5.90 (s, 1H), 4.19 (t, 2H, J=6.6 Hz), 4.16 (t, 2H, J=6.8 Hz), 4.02 (s, 3H), 3.81 (s, 3H, 3.17 (s, 1H). 13CNMR (300 MHz, CDCl3): δ=149.42, 148.11, 147.57, 146.58, 136.95, 135.43, 126.83, 121.04, 119.69, 111.48, 109.50, 107.92, 107.26, 101.65, 100.93, 71.34, 65.05, 55.94, 55.89.

Example 4

Synthesis of Cleistanthin A using (2-(1,3-Dioxolane-2-yl)-4,5-dimethoxy phenyl)(benzo(d)(1,3)dioxol-5-yl)-methanol (prepared as per the present invention):

Sealed tube was charged with (2-(1,3-Dioxolane-2-yl)-4,5-dimethoxy phenyl)(benzo(d)(1,3)dioxol-5-yl)-methanol (prepared as per any one of the examples 1-3) (0.30 g, 0.833 mmole), diethyl acetylinedicarboxylate (0.141 g, 0.833 mole), dichloromethane (0.4 ml) and glacial acetic acid (0.242 ml) and mixture was heated at 140° C. for 1 hour. After completion of reaction as judged by TLC (50:50, EtOAc:Hexane), reaction mixture was cooled to room temperature, diluted with dichloromethane (10 ml), washed with 5% sodium bicarbonate solution (3×10 ml), organic layer was dried over anhydrous sodium sulfate, filtered and concentrated. The crude reaction mass was purified by flash column chromatography over silica gel using EtOAc:hexane (15:85) to afford diethyl 1-(3',4'-methylenedioxyphenyl)-4-hydroxy-6,7-dimethoxynaphthalene-2,3-dicarboxylate as white solid 0.3 g (75%).

Two necked round bottom flask was charged with lithium aluminum hydride (0.032 g, 0.852 mmol) and anhydrous tetrahydrofuran (4 ml) and the mixture was cooled to 0° C. with stirring. To this suspension, a solution of diethyl 1-(3',4'-methylenedioxyphenyl)-4-hydroxy-6,7-dimethoxynaphthalene-2,3-dicarboxylate (0.200 g, 0.426 mmol) in tetrahydrofuran (4 ml) was added drop wise and stirring was continued for 2 hours. After completion of reaction as judged by TLC (1:9, MeOH:DCM), reaction mixture was quenched with saturated sodium sulfate solution and extracted with n-butanol (4×20 mL). Organic layer was dried over anhydrous sodium sulfate, filtered and concentrated under reduced pressure. The crude residue was purified by flash column chromatography over silica gel to give yellow solid 9-(3',4'-Methylenedioxyphenyl)-4-hydroxy-6,7-dimethoxynaphtho[2,3-c]furan-1(3H)-one 0.07 g (85%).

To a flame dried three necked round bottom flask (250 ml), 9-(3',4'-methylenedioxyphenyl)-4-hydroxy-6,7-dimethoxynaptho[2,3-c]furan-1(3H)-one compound (1.2 g 0.0031 mole), and methylene dichloride (100 ml) were added and stirred to dissolve completely. Then 2-O-Acetyl-3,4-dimethoxy-α-D-bromoxylopyranose (1.8 g, 0.0063 mole), tetra butyl ammonium bromide (0.49 g, 0.00151 mole) and 1 N sodium hydroxide solution (4 ml) were added in above solution. Reaction mass was kept for digestion under stirring for 2 hours, conversion was checked by TLC (MeOH:MDC, 0.5:9.5) and the conversion if found unconverted then digestion continued till conversion was complete. After completion of reaction, the reaction mass was washed with 1% sodium bicarbonate solution. After layer separation, methylene dichloride was concentrated to give solid 1.62 gms (yield 55%) of Cleistanthin A acetate.

In a clean dry three necked round bottom flask cleistanthin A acetate (1.26 g, 0.0027 mole), potassium carbonate catalytic amount (0.1 g, 0.00072 mole) and methanol (100 ml) were added & stirred well for 1 Hr at temperature 25° C. Reaction was monitored by TLC and HPLC. After completion of reaction, the reaction mass was quenched by water and extracted with ethyl acetate (2×30 ml) to get the final product. Ethyl acetate was concentrated to get pure 1.2 gm (yield 97%) of cleistanthin A.

The NMR details cleistanthin A were as follows:

$^1$HNMR (CDCl$_3$, 300 MHz): =7.92 (s, 1H), 7.05 (d, 1H, J=1.5 Hz), 6.94 (dd, 1H, J=1.2, 7.8 Hz), 6.83-6.78 (m, 2H), 6.07 (d, 1H, J=14.1 Hz), 6.06 (d, 1H, J=14.4 Hz), 5.49 (d, 1H, J=14.7 Hz), 5.42 (d, 1H, J=14.7 Hz), 5.10 (d, 1H, J=5.7 Hz), 4.10 (dd, 1H, J=2.4, 12.0 Hz), 4.04 (s, 3H), 3.95-3.88 (m, 1H), 3.80 (s, 3H), 3.68 (s, 3H), 3.49 (s, 3H), 3.45 (dd, 1H, J=Hz), 3.93-3.30 (m, 3H). $^{13}$CNMR (300 MHz, CDCl$_3$): =169.75, 151.77, 150.15, 147.41, 144.09, 135.84, 130.61, 128.90, 128.87, 128.35, 126.79, 123.55, 119.13, 110.68, 108.10, 106.04, 103.45, 101.16, 101.02, 82.10, 78.20, 71.13*, 71.11*, 67.26, 61.13, 60.01, 57.91, 56.15, 55.76.

What is claimed is:

1. A method for preparing a compound of formula D:
providing a solution of a compound of formula C:
sonicating the solution; and
contacting the solution with an aryl aldehyde solution and an alkyl lithium reagent under sonication to form the compound of formula D;
wherein:

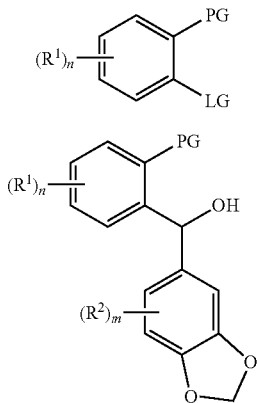

m is 0, 1, 2, or 3;
n is 0, 1, 2, 3, or 4;
each $R^1$ is independently selected from halogen, —NO$_2$, —CN, or -L-R;
each $R^2$ is independently selected from halogen, —NO$_2$, —CN, or -L-R;
each L is independently a covalent bond or an optionally substituted bivalent C$_{1-6}$ hydrocarbon chain, wherein one or two methylene units of L is optionally and independently replaced by —O—, —S—, —N(R)—, —C(O)—, —C(S)—, —C(O)N(R)—, —N(R)C(O)N(R)—, —N(R)C(O)—, —N(R)C(O)O—, —OC(O)N(R)—,—S(O)—,—S(O)$_2$—, —S(O)$_2$N(R)—, —N(R)S(O)$_2$—, —OC(O)—or —C(O)O—;

each R is independently hydrogen or an optionally substituted group selected from C$_{1-6}$ aliphatic, phenyl, a 3-8 membered monocyclic saturated or partially unsaturated carbocyclic ring, an 8-10 membered bicyclic saturated, partially unsaturated, or aromatic carbocyclic ring, a 3-8 membered monocyclic saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic saturated, partially unsaturated, or aromatic heterocyclic ring having 1-4 heteroatoms independently selected from nitrogen, oxygen, or sulfur, or:

two R groups on the same nitrogen are taken together with their intervening atoms to form a 3-8 membered saturated, partially unsaturated, or aromatic ring having 1-4 heteroatoms independently selected from nitrogen, oxygen, or sulfur; and each PG is independently selected from —CH(OR$^3$), 2-(1,3-dioxolanyl) or 2-(1,3-dioxanyl);

$R^3$ is an optionally substituted aliphatic group; and
LG is halogen,
wherein the sonication and contacting steps take place between 0-25° C. or at a room temperature.

2. The method of claim 1, wherein LG is bromine or iodine.

3. The method of claim 1, wherein the alkyl lithium reagent is n-butyllithium.

4. The method of claim 1, wherein the aryl aldehyde is pipronal or optionally substituted pipronal.

5. The method of claim 1, wherein the solution of the compound of formula C and the aryl aldehyde comprises a non-polar, aprotic solvent selected from diethyl ether, methyl-tert-butylether, tetrahydrofuran, dioxane, hexane, or cyclohexane.

6. The method of claim 1, wherein PG is 2-(1,3-dioxolanyl).

7. The method of claim 1, further comprising:
contacting the compound of formula D with a compound of formula E:

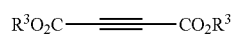

under conditions effective to form a compound of formula F:

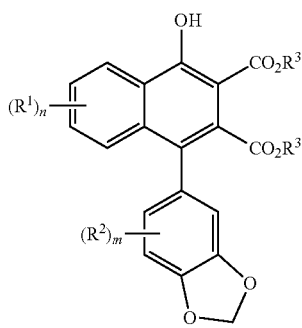

wherein:
each $R^3$ is an optionally substituted $C_{1-6}$ aliphatic.

8. The method of claim 7, wherein each $R^3$ is ethyl.

9. The method of claim 8, wherein PG is 2-(1,3-dioxolanyl).

10. The method of claim 9 further comprising heating the compound of formula D and the compound of formula E in acetic acid.

11. The method of claim 10, wherein the heating is conducted at about 120° C. to about 140° C.

12. The method of claim 7, further comprising contacting the compound of formula F with a metal hydride to form a compound of formula III:

III

13. The method of claim 12, wherein the metal hydride is lithium aluminum hydride.

14. The method of claim 12 further comprising:
contacting the compound of formula III with a pyranose of formula V:

V under conditions effective to form a compound of formula IV:

IV or a pharmaceutically acceptable salt thereof;
wherein:
each of $R^4$, $R^5$ and $R^6$ is independently hydrogen, $R^7$, or —C(O)$R^7$; and
each $R^7$ is independently an optionally substituted $C_{1-6}$ aliphatic group or a suitable hydroxyl protecting group.

15. A method for preparing cleistanthin A comprising contacting compound of formula IV obtained by method of claim 14 with an alkali and a solvent to form Cleistanthin A (I).

16. The method according to claim 15, wherein the alkali is potassium carbonate and solvent is methanol.

* * * * *